United States Patent [19]
Roth

[11] Patent Number: 5,263,965
[45] Date of Patent: Nov. 23, 1993

[54] MANUAL COMPRESSION AID AND METHOD

[76] Inventor: Robert A. Roth, 1136 St. Mary's La., Festus, Mo. 63028

[21] Appl. No.: 646,812

[22] Filed: Jan. 28, 1991

[51] Int. Cl.$^5$ ............................................. A61B 17/12
[52] U.S. Cl. .................................................. 606/201
[58] Field of Search .................. 606/201, 203, 204; 128/67, 155, 887; 604/308, 180, 179

[56] References Cited

U.S. PATENT DOCUMENTS

| | | | |
|---|---|---|---|
| 1,338,578 | 4/1920 | Maeda | 606/201 |
| 3,779,249 | 12/1973 | Semler | 606/201 |
| 3,884,240 | 5/1975 | Gilman | 606/201 |
| 4,182,338 | 1/1980 | Stanulis | 606/203 |
| 4,308,861 | 1/1982 | Kelly | 606/204 |
| 4,557,262 | 12/1985 | Snow | 606/204 |
| 4,572,182 | 2/1986 | Royse | 604/116 |
| 4,579,120 | 4/1986 | MacGregor | 604/180 |
| 4,632,671 | 12/1986 | Dalton | 604/180 |
| 4,829,995 | 5/1989 | Metters | 128/155 |

FOREIGN PATENT DOCUMENTS 8100202  2/1981  World Int. Prop. O. .......... 604/204

Primary Examiner—Stephen C. Pellegrino
Assistant Examiner—William Lewis
Attorney, Agent, or Firm—Polster, Lieder, Woodruff & Luccchesi

[57] ABSTRACT

A manual compression aid for applying direct pressure to arterial and venous punctures to obtain hemostasis includes an integrally formed pressure applicator having a relatively flat first surface adapted for contact with a human body and having a user manipulable member for holding the pressure applicator and for applying force thereto. In one embodiment, the user manipulable member is a peg extending upwardly from the first surface. The peg not only is manipulatable by a user to manually apply pressure to a puncture site, but also functions to receive a separate cylindrical weight. The weight is pivotally mounted on the peg so that it can swivel. A stretchable bandage is used to secure and stabilize the weight in place. The bandage, being held above the puncture by the pressure applicator and the weight, also acts to supply pressure to the puncture site.

28 Claims, 2 Drawing Sheets

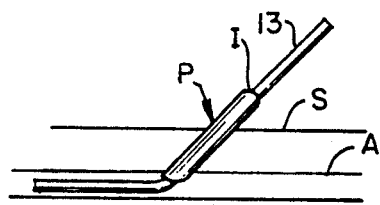
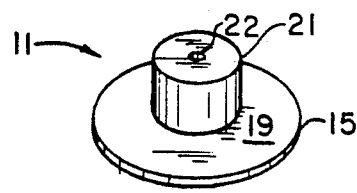
FIG. 2.  FIG. 1A.
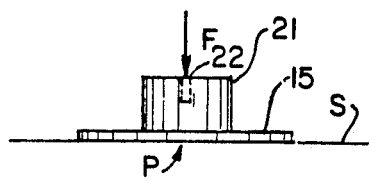
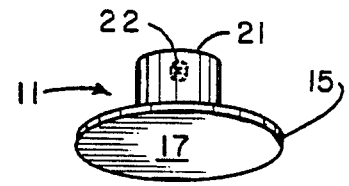
FIG. 3.  FIG. 1B.
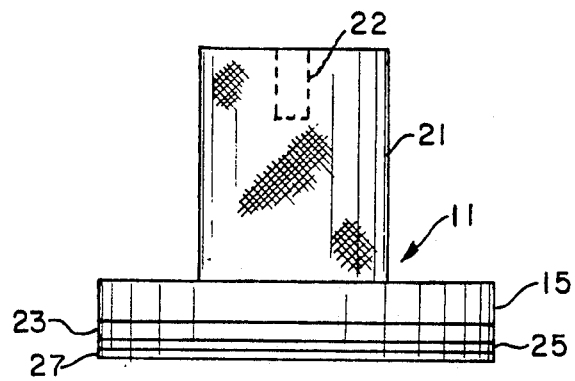
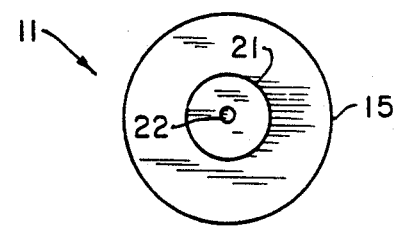
FIG. 4.  FIG. 5.
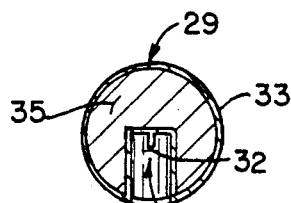
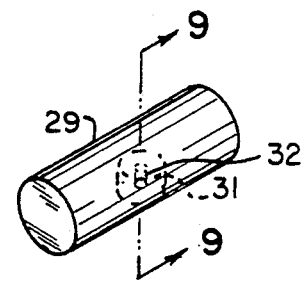
FIG. 9.  FIG. 6.
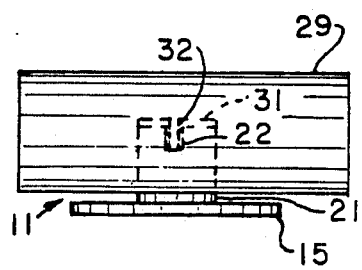
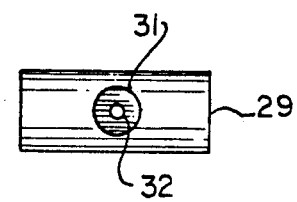
FIG. 8.  FIG. 7.

MANUAL COMPRESSION AID AND METHOD

BACKGROUND OF THE INVENTION

This invention relates generally to the field of arterial and venous catheterization, and more particularly to devices and methods for achieving hemostasis following catheterization.

Catheterization is a fairly common procedure for purposes of diagnosing and treating diseases and other conditions of the human body. Cardiac catheterization is an example of such a procedure. In such a procedure a catheter is inserted into a suitable artery or vein (such as the femoral artery), and then advanced to the proper site inside the human body. After the procedure is completed, the catheter is removed. Bleeding at the puncture site can be a significant medical problem once the catheter is removed, particularly considering the relatively high pressures in the vessels involved. Bleeding at the puncture site can be an even more significant problem when thrombolytic (clot dissolving) agents are used in the procedure. When these agents are used, the patient almost always experiences some type of bleeding problems after removal of the catheter.

Heretofore, standard practice has been to apply direct manual pressure to the puncture site to achieve initial hemostasis and to thereafter apply continuing pressure by means of certain mechanical devices such as bandages, sandbags, or clamps. These particular devices could be improved since they do not adequately localize the applied pressure in the immediate vicinity of the puncture, they are subject to shifting as the patient moves, some tend to be uncomfortable, and many severely limit movement of the patient.

A device called Hold, manufactured by Pressure Products, Inc. and distributed by Cardio Source of Rancho Palos Verdes, California, has been devised to overcome some of these problems, but the Hold device could also be improved. The Hold device uses a foam hemisphere which is placed over the puncture site after initial hemostasis has been achieved. The foam hemisphere is held in place by an elastic strap which, because of its elasticity provides some measure of pressure to the foam hemisphere and the puncture site. Because of the materials involved, however, the actual pressure applied by the Hold device is less than optimal.

SUMMARY OF THE INVENTION

Among the various objects and features of the present invention may be noted the provision of an improved device and method for obtaining hemostasis.

Another object is the provision of such a device and method in which pressure is applied in precisely the desired location to achieve hemostasis.

A further object is the provision of such a device and method which focuses the pressure at the puncture site.

A fourth object is the provision of such a device and method which readily adapts to patients of different sizes and shapes.

A fifth object is the provision of such a device and method which is held securely in place, even when the patient moves.

A sixth object is the provision of such a device and method which tends to be more comfortable for the patient and allows greater patient movement.

A seventh object is the provision of such a device and method which provides optimal pressure to the puncture site.

An eighth object is the provision of such a device and method which is durable in construction, yet relatively inexpensive.

A ninth object is the provision of such a device and method which allows easier manual application of pressure to the puncture site.

A tenth object is the provision of such a device and method which effects hemostasis faster and more effectively.

Other objects and features will be in part apparent and in part pointed out hereinafter.

Briefly, in a first aspect, a manual compression aid of the present invention is adapted for applying direct manual pressure to arterial and venous punctures to obtain hemostasis. The manual compression aid includes a relatively flat, rigid disk having a first surface adapted for contact with a human body and having a second, opposite surface. The disk has a predetermined diameter selected to ensure that a puncture, such as that made by the introduction of a catheter into a human body, and the area of the body immediately surrounding the puncture, are covered by the first surface of the disk when the compression aid is applied to the puncture. A peg extends upwardly from the second surface of the disk, the peg having a diameter substantially less than the diameter of the rigid disk. The peg is fixedly secured to the disk and provides structure for manually holding and manipulating the compression aid. A medical professional may grasp the compression aid by the peg, place the first surface of the disk over the puncture, and apply pressure to the site of the puncture by manually applying pressure to the compression aid.

In a second aspect of the present invention, a prepackaged manual compression aid kit includes an integrally formed pressure applicator having a rigid disk and a peg extending axially from one surface of the rigid disk, the opposite surface of the rigid disk being adapted to be placed on a puncture site on a human body, and a weight supplying member having a predetermined weight. The weight supplying member is adapted to be pivotally secured to the pressure applicator. The kit also includes a container in which the pressure applicator and the weight supplying member are removably disposed.

In a third aspect, a manual compression aid of the present invention is adapted for applying direct manual pressure to arterial and venous punctures to obtain hemostasis. The manual compression aid includes a relatively flat, rigid disk for manually holding and manipulating the compressions aid. A compression peg extends from the disk, said peg having a diameter selected to cover a puncture site, such as that made by the introduction of a catheter into a human body, and the area of the body immediately surrounding the puncture. The peg is fixedly secured to the disk. A medical professional may grasp the compression aid by the disk, place the distal surface of the peg over the puncture, and apply pressure to the site of the puncture by manually applying pressure to the compression aid.

A method of the present invention includes the steps of manually applying a pressure applicator to the puncture site, which pressure applicator has a rigid disk with a surface adapted to be disposed against the puncture site and a peg sized to permit easy manipulation of the pressure applicator by a user, pivotally mounting a weight supplying member on the peg of the pressure applicator, the weight supplying member having an orifice sized to accept the peg, and securing the pressure applicator and weight supplying member in place by means of a stretchable bandage secured to the human body and stretched over the weight supplying member.

In a second aspect, the method of the present invention includes the steps of manually applying a pressure applicator to the puncture site, which pressure applicator has a rigid disk sized to permit easy manipulation of the pressure applicator by a user and a peg sized to cover the puncture site, pivotally mounting a weight supplying member on the pressure applicator, the weight supplying member having an orifice sized to accept a portion of the pressure applicator, and securing the pressure applicator and weight supplying member in place by means of a stretchable bandage secured to the human body and stretched over the weight supplying member.

BRIEF DESCRIPTION OF THE DRAWINGS

FIG. 1A is a perspective view from above illustrating a pressure applicator comprising part of the present invention;

FIG. 1B is a perspective view of the pressure applicator of FIG. 1 from below;

FIG. 2 is a sectional view illustrating the placement of a catheter in a human body;

FIG. 3 is a simplified schematic illustrating the use of the pressure applicator of FIG. 1 immediately after removal of the catheter of FIG. 2;

FIG. 4 is an elevation, on an enlarged scale, of one embodiment of the pressure applicator of FIG. 1;

FIG. 5 is a top plan of the pressure applicator of FIG. 1;

FIG. 6 is a perspective view of a weight applying member used with the pressure applicator of FIG. 1 to achieve long-term hemostasis;

FIG. 7 is a bottom plan of the weight applying member of FIG. 6;

FIG. 8 is a side elevation of the pressure applicator of FIG. 1 in combination with the weight applying member of FIG. 6;

FIG. 9 is a cross-sectional view taken along line 9—9 of FIG. 6;

Similar reference characters indicate similar parts throughout the several views of the drawings.

DESCRIPTION OF THE PREFERRED EMBODIMENT

Figure 10:
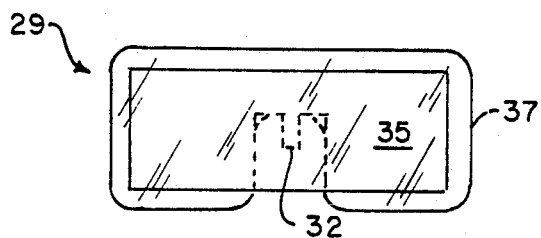
FIG. 10 is an elevation illustrating a second embodiment of the weight applying member of FIG. 6.
Figure 12:
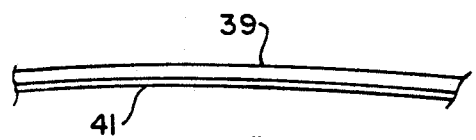
FIG. 12 is a side elevation illustrating a bandage used in the combination of FIG. 11.

Turning now to the drawings, a manual compression aid 11 (FIGS. 1A and 1B) of the present invention is adapted for applying direct manual pressure to arterial and venous punctures to obtain hemostasis. The need for such a device arises out of medical procedures such as that illustrated in FIG. 2 in which a catheter 13 in introduced through a puncture P in the skin S of a human patient to a vein or artery, A, such as a femoral artery. The catheter passes through an introducer I, which can be a needle or other hollow device, into the vein or artery. The catheter 13 is fed through the vein or artery to the desired position in the human body for diagnostic or treatment purposes. Such procedures and associated devices are well known.

When the introducer and catheter are removed, at the end of the procedure, significant and potentially serious bleeding can occur at puncture site P unless hemostasis is achieved. Achieving such hemostasis is accomplished by use of manual compression aid 11.

The manual compression aid includes a relatively flat, rigid disk 15 having a first surface 17 (FIG. IB) adapted for contact with a human body (specifically skin S) and a second, opposite surface 19. (For an alternative way of using manual compression aid 11, see FIG. 14 and the accompanying description.) The disk 15 has a predetermined diameter selected to ensure that a puncture, such as the one made at puncture site P, and the area of the body immediately surrounding the puncture are covered by first surface 17 when compression aid 11 is applied to the puncture. By way of example, a diameter of approximately 1⅜ to 2 inches has been found to be satisfactory for adult patients, while a disk diameter of approximately one inch has been found to be satisfactory for pediatric patients. Of course, diameters falling outside this range (for example, from approximately ½" to approximately 4") are also acceptable. Disk 15 may have a range of thicknesses, for example, its thickness can range from 1/32" to 3" or greater. The disk 15 shown has a thickness of ¼". Although the disk shown is circular, oval disks and disks of similar shape would also work.

A peg 21 extends upwardly from top surface 19 of the disk. As will become apparent, peg 21 serves a dual purpose. The peg itself has a diameter substantially less than the diameter of the rigid disk. For example, for adult patients the peg has a diameter of approximately 1¼ inches while the peg used with pediatric patients has a diameter of approximately ⅝ inch. This is not meant to exclude larger and smaller pegs, which may range in diameter from 3/16" to 2". The height of peg 21 may vary from approximately 3/16" inch to approximately 2" or greater, depending upon the size of the manual compression aid.

The peg is fixedly secured to the top surface 19 of disk 15 and preferably is formed as an integrally molded part with the disk. For example, the manual compression aid 11 preferably is a single part formed by injection molding from a suitable plastic such as polycarbonate.

Peg 21 functions as a handle for manually holding and manipulating the compression aid immediately after removal of the catheter 13 and introducer I. To use manual compression aid 11, a medical professional grasps compression aid 11 by peg 21, places bottom surface 17 over the puncture site P, and applies pressure to the puncture site by manually applying pressure to the compression aid as indicated by the arrow labelled F in FIG. 3. As explained below in connection with FIG. 14, the compression aid may also be used in the opposite orientation from that shown in FIGS. 1 and 3.

As can be seen in the FIGS., peg 21 optionally includes an orifice 22 sized to accept a corresponding pin (see FIGS. 6-9 for a description).

Although manual compression aid 11 may be made of a single piece of molded plastic, other variations are contemplated. For example, bottom surface 17 may have suitably secured thereto (by adhesive, for example) a resilient foam pad 23 (FIG. 4) generally coextensive with the bottom surface to improve patient comfort. Foam pad 23 may optionally be absorbent to prevent small amounts of blood from seeping out from under manual compression aid 11.

Also shown in FIG. 4 (on an exaggerated scale) is a layer of adhesive 25 covering the bottom of foam pad 23. The adhesive layer is in turn covered by a peel-off strip or layer 27. When the medical professional is ready to use manual compression aid 11, he/she simply removes the peel-off strip, thereby exposing the layer of adhesive, and places the compression aid, bottom side down, over the puncture site P. The adhesive holds the compression aid in place so as to resist undesired movement of the compression aid after placement over the puncture site.

Also shown in FIG. 4 is the knurled surface of peg 21. This knurling is provided to facilitate grasping and manipulation of the manual compression aid. However, peg 21 also functions as a pivot point (as is explained below), so it is not desirable that the peg 21 be excessively rough.

FIG. 5 illustrates the fact that both the rigid disk 15 and peg 21 are circular in cross section. It is particularly significant that the peg be circular in cross section, since this promotes the pivot point action mentioned above. However, other configurations of both disk and peg are possible and intended to fall within the broader scope of the present invention.

It is also desirable, although not critical to the present invention, that at least rigid disk 15 be transparent. This allows the user to tell at a glance whether bleeding is still occurring at the puncture site P and to estimate the amount. If such bleeding is occurring, the user, upon seeing this fact through the transparent disk, can stop the bleeding by applying more pressure to the compression aid.

Alternatively, disk 15 may have a "bull's-eye" appearance from the medical professional's perspective (see description below in connection with FIG. 15), resulting from a series of rings of translucent or opaque foam pad and/or adhesive separated by a clear material or air, so that through the clear disk the user sees the bull's-eye pattern centered on the axis of the manual compression aid.

As can be seen from the above description, initial hemostasis may be readily achieved by manually pressing down on manual compression aid 11 over the puncture site P. However, it is not feasible for the medical professional to remain with the patient for the extended period, such as one hour, two hours or more, which is necessary to achieve complete hemostasis. The manual compression aid of the present invention further includes, therefore, a separate member 29 designed to provide the desired long-term pressure to the puncture site.

Member 29 has a predetermined weight selected to exert the desired pressure. For example, for adult patients, the predetermined weight is preferably approximately 3 ½ to approximately 4 pounds, while for pediatric patients it is preferably approximately ½ to approximately 1 pound. Other weights outside this range are also intended to be within the scope of this invention.

Member 29 is preferably generally cylindrical, as shown in FIG. 6, and it includes a round opening 31 (best shown in FIG. 7) sized to accept peg 21 for pivotal movement around the axis of the peg (see FIG. 8). Concentric with opening 31 is a pin 32 sized to fit within opening 22 in peg 21. When placed on peg 21, member 29 continuously applies the predetermined weight to the vicinity of the puncture. Pin 32 and orifice 22 cooperate to center the peg and member 29 with respect to each other.

Member 29 is preferably between approximately ⅜" and approximately 1¾" in diameter, and between approximately 2" and approximately 3½" in length. This particular length is selected to correspond to the width of bandages commonly used in hospitals. More generally, member 29 may have a diameter between approximately ¼" and approximately 4" and a length from approximately 1" to approximately 6".

Member 29 is preferably formed of metal so as to provide the desired weight in the smallest possible volume. To protect the metal from the various chemicals encountered, it is preferably provided with a non-metallic coating, such as the coating 33 shown in FIG. 9. For example, a plastic such as polyethylene or vinyl provides a suitable coating 33 for the metal core 35 of member 29. Alternatively, member 29 may be composed of stainless steel.

Alternatively, the metal core 35 of member 29 may be disposed in a removable, replaceable cover or bag 37 (see FIG. 10) made of a suitable plastic such as polyethylene. This removable cover protects the metal core while at the same time preventing cross contamination between patients. After the manual compression aid is used or one patient, the removable cover is simply removed and discarded. A new cover is then placed over metal core 35 before the manual compression aid is used on the next patient.

Figure 11:
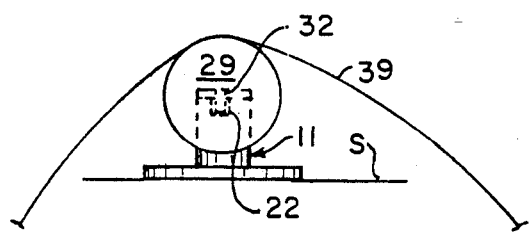
FIG. 11 is a simplified schematic illustrating long-term use of the pressure applicator of FIG. 1 and the weight applying member of FIG. 6.

As can best be seen in FIG. 11, member 29 is disposed a predetermined distance above the body of the patient. As a result, if the bandages 39 which are disposed over the manual compression aid to stabilize it and hold it in place are in tension, then a pressure resulting from that tension is applied by manual compression aid to the puncture site. The elevation of the bandage above the puncture site provides additional leverage for increasing the applied pressure. In fact, with this increased leverage, the bandages themselves, without the weight of member 29 may in some instances provide enough pressure for hemostasis. Although only a single bandage 39 is shown, it is preferred that a pair of bandages crisscross the manual compression aid. The bandages are secured to the patient's body in one of a number of conventional ways. The bandages are of a standard width, such as four inches, which corresponds with the length o the weight applying member 29.

In one embodiment, the bandages include an adhesive layer 41 for securement to the body and/or to the manual compression aid 11. This bandage stabilizes the placement of the weight applying member 29 above the puncture site P.

Figure 13:
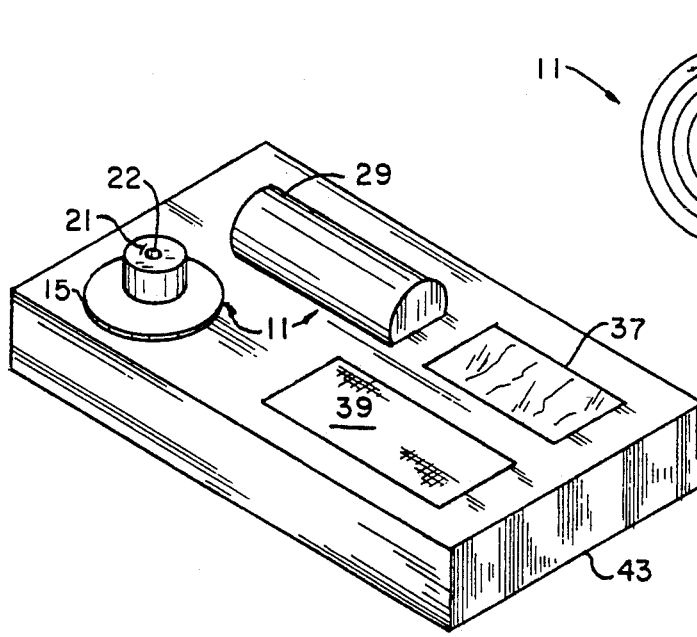
FIG. 13 is a perspective view of a kit including the pressure applicator of FIG. 1 and the weight applying member of FIG. 6.

To facilitate use of the manual compression aid 11 of the present invention, it can be packaged in kit form, as shown in FIG. 13. At a minimum, the kit includes the manual pressure applicator consisting of disk 15 and peg 21, and weight applying member 29. If the disposable cover 37 is used with member, the cover may be included in the kit as well. The desired number of bandages 39 may also be included. The components of the kit are removably disposed in a suitable container or tray 43, which is preferably sterilizable so that the kit may be used in a sterile field.

The method of the present invention is therefore seen to include the steps of manually applying the pressure applicator made up of disk 15 and peg 21 to the puncture site P until initial hemostasis is achieved. Weight supplying member 29 is then pivotally mounted on peg 21. This combined structure is then secured in place by means of stretchable bandage 39 suitably secured to the patient's body and stretched over the weight supplying member.

Figure 14:
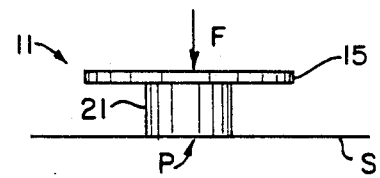
FIG. 14 is an elevation similar to FIG. 3 illustrating another method of using the manual compression aid of the present invention.

Turning to FIG. 14, it can be seen that manual compression aid 11 may be inverted from the position used in FIG. 3 and still work satisfactorily. In this inserted position, the aid is held by disk 15 by the medical professional, and the distal end of peg 21 is adapted for contact with a human body (specifically skin S). When used in this way, peg 21 has a predetermined diameter selected to ensure that a puncture, such as the one made at puncture site P, and the area of the body immediately surrounding the puncture are covered by the distal surface of the peg when compression aid 11 is applied to the puncture.

Thus, it can be seen that the manual compression aid of the present invention allows the user to select which of two different pressures to apply to the puncture site by the expedient of inverting the manual compression aid.

Figure 15:
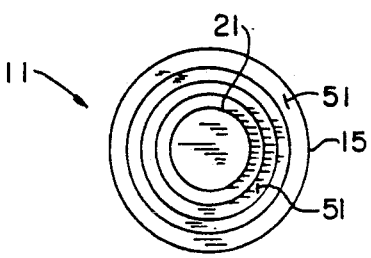
FIG. 15 is a top plan of an alternative embodiment of the manual compression aid of the present invention.

Turning to FIG. 15, there is shown the bull's-eye configuration discussed above in which a series of rings 51 of foam pad/adhesive are centered with respect to flat disk 15 to give the appearance of a bull's-eye to the user. This configuration allows the user to observe blood seeping between adjacent rings, thereby indicating the need to apply additional pressure to achieve hemostasis.

In view of the above it will be seen that the various objects and features of the present invention are achieved and other advantageous results obtained. It is not intended that the present invention be limited by the precise descriptions or drawings thereof contained herein. Rather the invention is to be construed in scope only with reference to the following claims.

What is claimed is:

1. A manual compression aid for applying direct pressure to arterial and venous punctures to obtain hemostasis, comprising:

a relatively flat, rigid disk having a first surface adapted for contact with a human body and having a second, opposite surface, said disk having a predetermined diameter selected to ensure that a puncture, such as that made by the introduction of a catheter into a human body, and the area of the body immediately surrounding the puncture, are covered by the first surface of the disk when the compression aid is applied to the puncture;

a peg extending upwardly from the second surface of the disk, said peg having a diameter substantially less than the diameter of the rigid disk, said peg being fixedly secured to the disk and providing means for manually holding and manipulating the compression aid;

whereby a medical professional may grasp the compression aid by the peg, place the first surface of the disk over the puncture, and apply pressure to the site of the puncture by manually applying pressure to the compression aid;

wherein the relatively flat, rigid disk has secured to the first surface thereof a resilient pad generally coextensive with the first surface.

2. The manual compression aid as set forth in claim 2 wherein the resilient pad has a layer of adhesive thereon disposed for contact with the human body when the compression aid is put in place so as to assist in holding the compression aid in place on the human body.

3. A manual compression aid for applying direct pressure to arterial and venous punctures to obtain hemostasis, comprising:

a relatively flat, rigid disk having a first surface adapted for contact with a human body and having a second, opposite surface, said disk having a predetermined diameter selected to ensure that a puncture, such as that made by the introduction of a catheter into a human body, and the area of the body immediately surrounding the puncture, are covered by the first surface of the disk when the compression aid is applied to the puncture;

a peg extending upwardly from the second surface of the disk, said peg having a diameter substantially less than the diameter of the rigid disk, said peg being fixedly secured to the disk and providing means for manually holding and manipulating the compression aid;

whereby a medical professional may grasp the compression aid by the peg, place the first surface of the disk over the puncture, and apply pressure to the site of the puncture by manually applying pressure to the compression aid;

further including a layer of adhesive disposed between the first surface of the disk and the human body when the compression aid is in use for securing the compression aid in place above the puncture.

4. The manual compression aid as set forth in claim 3 wherein the adhesive layer forms part of an adhesive backed foam pad secured to the first surface of the disk, said foam pad being generally coextensive with the first surface.

5. The manual compression aid as set forth in claim 3 further including a peel-off strip covering the adhesive layer until the manual compression aid is ready to be used.

6. A manual compression aid for applying direct pressure to arterial and venous punctures to obtain hemostasis, comprising:

a relatively flat, rigid disk having a first surface adapted for contact with a human body and having a second, opposite surface, said disk having a predetermined diameter selected to ensure that a puncture, such as that made by the introduction of a catheter into a human body, and the area of the body immediately surrounding the puncture, are covered by the first surface of the disk when the compression aid is applied to the puncture;

a peg extending upwardly from the second surface of the disk, said peg having a diameter substantially less than the diameter of the rigid disk, said peg being fixedly secured to the disk and providing means for manually holding and manipulating the compression aid;

whereby a medical professional may grasp the compression aid by the peg, place the first surface of the disk over the puncture, and apply pressure to the site of the puncture by manually applying pressure to the compression aid;

wherein the disk is between approximately 1' and approximately 2¼' in diameter.

7. A manual compression aid for applying direct pressure to arterial and venous punctures to obtain hemostasis, comprising:

a relatively flat, rigid, transparent disk having a first surface adapted for contact with a human body and having a second, opposite surface, said disk having a predetermined diameter selected to ensure that a puncture, such as that made by the introduction of a catheter into a human body, and the area of the body immediately surrounding the puncture, are covered by the first surface of the disk when the compression aid is applied to the puncture;

a peg extending upwardly from the second surface of the disk, said peg having a diameter substantially less than the diameter of the rigid disk, said peg being fixedly secured to the disk and providing means for manually holding and manipulating the compression aid; and, a series of non-transparent rings concentric with and secured to the disk so as to present to the user a bulls-eye appearance, whereby a medical professional may grasp the compression aid, by he peg, place the first surface of the disk over the puncture, and apply pressure to the site of the puncture by manually applying pressure to the compression aid.

8. A manual compression aid for applying direct pressure to arterial and venuous punctures to obtain hemostasis, comprising:

a relatively flat, rigid disk having a first surface adapted for contact with a human body and having a second, opposite surface, said disk having a predetermined diameter selected to ensure that a puncture, such as that made by the introduction of a catheter into a human body, and the area of the body immediately surrounding the puncture, are covered by the first surface of the disk when the compression aid is applied to the puncture;

a peg extending upwardly from the second surface of the disk, said peg having a diameter substantially less than the diameter of the rigid disk, said peg being fixedly secured to the disk and providing means for manually holding and manipulating the compression aid; and, a separate member having a predetermined weight adapted to be secured to the peg so as to continuously apply the predetermined weight to the vicinity of the puncture, said separate member including an orifice sized to receive the peg, whereby a medical professional may grasp the compression aid by the peg, place the first surface of the disk over the puncture, and apply pressure to the site of the puncture by manually applying pressure to the compression aid.

9. The manual compression aid as set forth in claim 8 wherein the peg includes a hole therein and the separate member includes a pin the orifice, said pin of the separate member being sized to fit in the hole of the peg when the peg is received in the orifice of the separate member.

10. The manual compression aid as set forth in claim 8 wherein the separate member is pivotally secured to the peg so as to swivel about an axis defined by the peg.

11. The manual compression aid as set forth in claim 8 wherein the separate member is cylindrical.

12. The manual compression aid as set forth in claim 11 wherein the cylindrical member is between approximately ½" and approximately 4' in diameter.

13. The manual compression aid as set forth in claim 11 wherein the cylindrical member is between approximately 1" and approximately 6" in length.

14. The manual compression aid for applying direct pressure to arterial and venous punctures to obtain hemostasis, comprising:

a relatively flat, rigid disk having a first surface adapted for contact with a human body and having a second, opposite surface, said disk having a predetermined diameter selected to ensure that a puncture, such as that made by the introduction of a catheter into a human body, and the area of the body immediately surrounding the puncture, are covered by the first surface of the disk when the compression aid is applied to the puncture;

a peg extending upwardly from the second surface of the disk, said peg having a diameter substantially less than the diameter of the rigid disk, said peg being fixedly secured to the disk and providing means for manually holding and manipulating the compression aid; and, a separate metallic member having a predetermined weight adapted to be secured to the peg so as to continuously apply the predetermined weight to the vicinity of the puncture, and a non-metallic coating covering the metal, whereby a medical professional may grasp the compression aid by the peg, place the first surface of the disk over the puncture, and apply pressure to the site of the puncture by manually applying pressure to the compression aid.

15. The manual compression aid as set forth in claim 14 wherein the separate member is disposed in a removable, replaceable cover.

16. The manual compression aid as set forth in claim 14 wherein the separate member weighs between approximately ½ pound and approximately 4 pounds.

17. The manual compression aid as set forth in claim 14 wherein the peg spaces the separate member a predetermined distance above the body.

18. The manual compression aid as set forth in claim 14 further including a bandage stretched over the separate member and secured to the body.

19. The manual compression aid as set forth in claim 18 wherein the bandage is secured to the body in tension so as to apply pressure to the puncture site.

20. The manual compression aid as set forth in claim 18 wherein the bandage is approximately 4" or less in width.

21. The manual compression aid as set forth in claim 18 wherein the bandage includes an adhesive surface for securement to the body, so that said bandage stabilizes the placement of the predetermined weight above the puncture site.

22. A prepackaged manual compression aid kit comprising an integrally formed pressure applicator having a rigid disk and a peg extending axially from one surface of the rigid disk, at least one surface of the pressure applicator being adapted to be placed on a puncture site on a human body, a weight supplying member having a predetermined weight, said weight supplying member being adapted to be pivotally secured to the pressure applicator, a container in which the pressure applicator and the weight supplying member are removably disposed, and, a disposable bag removably disposed in the container, said bag being fitted to cover the weight supplying member and protect it from contamination during use.

23. A method of applying pressure to an arterial or venous puncture site in a human body comprising:

manually applying a pressure applicator to the puncture site, said pressure applicator having a surface adapted to be disposed against the puncture site and a member sized to permit easy manipulation of the pressure applicator by a user;

pivotally mounting a weight supplying member on pressure applicator, the weight supplying member having an orifice sized to accept the pressure applicator; and securing the pressure applicator and weight supplying member in place by means of a stretchable bandage secured to the human body and stretched over the weight supplying member.

24. The method of applying pressure to a puncture site as set forth in claim 23 further including the step of manually holding the pressure applicator over the puncture site and applying manual pressure to the site by means of the pressure applicator for a period of time before mounting the weight supplying member on the peg of the pressure applicator.

25. The method of applying pressure to a puncture site as set forth in claim 23 wherein the pressure applicator and weight supplying member are held in place by the bandage for a period of time sufficient to obtain hemostasis.

26. The method of applying pressure to a puncture site as set forth in claim 23 wherein the bandage also applies pressure to the puncture site, which pressure is transmitted to the puncture site through the weight supplying means and the pressure applicator.

27. The method of applying pressure to a puncture site as set forth in claim 26 further including the step of adjusting the pressure applied to the puncture side by adjusting the tension of the bandage.

28. The method of applying pressure to a puncture site as set forth in claim 23 wherein the bandage is clear, further including the step of viewing the vicinity of the puncture site through a clear bandage to determine if hemostasis is being achieved.

* * * * *